US00PP29095P3

(12) United States Plant Patent
Yamaguchi

(10) Patent No.: US PP29,095 P3
(45) Date of Patent: Mar. 13, 2018

(54) ***MAHONIA* PLANT NAMED 'SPG-15-1'**

(50) Latin Name: *Mahonia hybida*
Varietal Denomination: cv. sPg-15-1

(71) Applicant: Seiju Yamaguchi, Mizunami (JP)

(72) Inventor: Seiju Yamaguchi, Mizunami (JP)

(73) Assignee: CP DELAWARE, INC., Mizunami (JP)

( * ) Notice: Subject to any disclaimer, the term of this patent is extended or adjusted under 35 U.S.C. 154(b) by 52 days.

(21) Appl. No.: 14/757,357

(22) Filed: Dec. 22, 2015

(65) Prior Publication Data

US 2017/0181347 P1 Jun. 22, 2017

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Keith O Robinson
(74) *Attorney, Agent, or Firm* — Penny J. Aguirre

(57) ABSTRACT

A new and distinct *Mahonia hybrida* plant is provided that forms attractive dark green spiny foliage. Yellow flowers are formed in the spring extending into the summer with reblooming again in about August through frost. The growth habit is upright, and the plant has been found to be hardy in U.S.D.A. Hardiness Zone No. 7 during observations to date. The plant is well suited for providing attractive ornamentation in the landscape.

1 Drawing Sheet

Botanical/commercial classification: *Mahonia hybida/ Mahonia* Plant cv. sPg-15-1.

SUMMARY OF THE INVENTION

The new cultivar of the present invention was created in Japan during 2000 at the residence of the inventor in a cultivated area tended by man. Unknown *Mahonia* plants were crossed. The seeds resulting from the pollination were sown and small plants were obtained which were physically and biologically different from each other. Selective study results in the identification of a single plant of the new cultivar.

It was found that the new *Mahonia* plant of the present invention (a) exhibits an upright growth habit,
(b) forms attractive narrow dark green spiny foliage,
(c) commonly forms yellow flowers in the spring extending into the summer and reblooms again in about August through frost, and
(d) is well suited for providing attractive ornamentation in the landscape.

The new cultivar can be grown to advantage as attractive ornamentation in parks, gardens, and residential settings. The plant has been found to be hardy in U.S.D.A. Hardiness Zone No. 7a during observations to date.

The new cultivar can be readily distinguished from previously known *Mahonia* cultivars, including 'Narihira' cultivar (non-patented) and the 'Winter Sun' cultivar (non-patented). More specifically, the foliage of the new cultivar is spinier and stiffer than that of the 'Narihira' cultivar, and the leaves are of a lesser width than that of the 'Winter Sun' cultivar.

The new cultivar has been found near Hickory, N.C., U.S.A., to reliably undergo asexual propagation from one generation to another by the rooting of softwood stem cuttings. Accordingly, the new cultivar undergoes asexual propagation in a true-to-type manner.

When propagated by the use of softwood stem cuttings in early summer, rooting commonly is initiated in approximately two weeks, and a fully rooted finished plants commonly are produced in approximately eight weeks.

The new cultivar has been named 'sPg-15-1', and will be marketed under the BEIJING BEAUTY Trademark.

BRIEF DESCRIPTION OF THE PHOTOGRAPH

The accompanying photograph shows, as nearly true as is reasonably possible, a typical flowering plant of the new cultivar in which the foliage and inflorescence are shown in detail. The illustrated plant was approximately eighteen months of age and was growing outdoors during September 2014 near Hickory, N.C., U.S.A.

DETAILED BOTANICAL DESCRIPTION

The following is a detailed description of eighteen month-old plants of the new cultivar. The chart used in the identification of colors is that of The Royal Horticultural Society (R.H.S. Colour Chart—1995) except where general color terms are to be accorded their ordinary color significance.

Botanical classification: *Mahonia hybrida.*

Plant: Evergreen Shrub.

*Growth habit.*—Upright.
*Growth rate.*—Typical and average.
*Height.*—Approximately 1.2 to 1.5 m on average.
*Width.*—Approximately 0.9 to 1.2 m on average.
*Roots.*—Fibrous network and 155A in coloration.
*Diseases and pests.*—Not tested.

Branches:

*Shape.*—Substantially round.
*Length.*—Commonly approximately 12 cm on average.

*Diameter.*—Commonly approximately 1 cm on average.

*Color.*—Near Greyed-Brown Group 199A.

*Texture.*—Somewhat rough.

*Branch angle.*—Approximately 20 degrees.

*Internode length.*—Somewhat irregular, and commonly 2.5 to 4 cm on average.

Foliage:

*Leaf shape.*—Lanceolate, imparipinnate (odd pinnate).

*Leaf arrangement.*—In whorls with opposite leaflets.

*Leaf apex.*—Acute.

*Leaf base.*—Attenuate.

*Leaf margins.*—Spiny, serrate with approximately ten serrations per side.

*Leaf length.*—Commonly approximately 10 cm on average for upper leaves and approximately 8 cm on average for lower leaves.

*Leaf width.*—Commonly approximately 1.5 cm on average at the base and approximately 5 mm on average at the apex.

*Leaf texture.*—Glabrous on upper and lower surfaces, and lustrous on the upper surface.

*Leaf color.*—Near Green Group 139A on the upper surface and near Yellow-Green Group 146B on the under surface.

*Leaf quantity.*—An average of 6 leaves per stem 12 cm in length.

*Fragrance.*—None noticeable.

*Petioles.*—Length: approximately 7.5 cm on average. Width: approximately 2 mm on average. Texture: glabrous. Color: near Green Group 138A.

*Ligules.*—None observed.

*Rachis.*—Round, an average of 20 cm in length and 2.5 mm in diameter, surface is glabrous and lustrous, color on young leaves; 144A, color on mature leaves; 146B.

Inflorescence:

*Time.*—Commonly commences in the spring (e.g. in about April) extending into the summer with reblooming again in approximately August through frost.

*Arrangement.*—Fascicles of racemes arranged in whorls with approximately 5 racemes per whorl on average emerging above leaf whorls above the new foliage growth for the duration of flowering with racemes open from bottom towards the apex and tightly packed, and with approximately 15 flowers per raceme.

*Type.*—Perfect and cup-shaped.

*Buds.*—Shape: globose. Length: approximately 3 mm on average. Diameter: approximately 3 mm on average. Color: near Yellow-Green Group 145A commonly changing to near Yellow-Green Group 154C prior to opening.

*Flower aspect.*—Outwardly facing on raceme with racemes commonly held at an approximately 30 to 40 degree angle from the stem.

*Flower fragrance.*—Mild, sweet.

*Lastingness of inflorescence.*—4 to 6 weeks from the opening of the lower flowers to the opening of the upper flowers of the raceme, individual flowers persist for an average of 1 to 2 days.

*Flower quantity.*—About 15 flowers per raceme, about 5 racemes per whorl, new whorls emerge just below foliar rosette for duration of flowering season.

*Flower diameter.*—Commonly approximately 6 mm on average.

*Flower depth.*—Commonly approximately 4 mm on average.

*Raceme size.*—Commonly approximately 15 cm in length and approximately 1.5 cm in diameter.

*Petals.*—Number: six arranged in two whorls of three petals. Shape: obovate and unfused. Length: approximately 5 mm on average. Width: approximately 3 mm on average. Apex: rounded to acute. Base: rounded to acute. Margin: entire. Color: near Yellow Group 11A. Surfaces: upper and lower surfaces glabrous.

*Gynoecium.*—Number: one pistil. Stigma: approximately 1 mm in length on average, approximately 1 mm in width on average, and near Yellow Group 11A in coloration. Ovary: approximately 1 mm in length on average, approximately 1 mm in width on average, and near Yellow-Green Group 145A in coloration.

*Androcoecium.*—Number: six stamen. Anthers: approximately 0.5 mm in length on average, approximately 1 mm in width on average, and near Yellow Group 11A in coloration. Pollen: none.

*Filaments.*—Approximately 2 mm in length on average, approximately 1 mm in width on average and near Yellow Group 11A in coloration.

*Fruit and seeds.*—None observed to date.

*Peduncle.*—Length: approximately 16 cm on average. Width: approximately 1 mm on average. Color: new Yellow-Green Group 144B.

*Pedicels.*—Length: approximately 3 mm on average. Width: approximately 1 mm on average. Color: near Yellow-Green Group 144B.

*Calyx.*—Commonly provided in two whorls of 3 petaloid sepals.

*Sepals.*—Number: three. Length: approximately 3 mm on average. Width: approximately 2.5 mm on average. Shape: obovate. Apex: rounded to acute. Base: rounded to acute. Texture: glabrous. Margin: entire. Color: near Yellow Group 11A on upper and lower surfaces. Surfaces: upper and lower surfaces glabrous.

The new .'sPg-15-1' cultivar has not been observed under all possible environmental conditions to date. Accordingly, it is possible that the phenotypic expression may vary somewhat with changes in light intensity and duration, cultural practices, and other environmental conditions.

I claim:

1. A new and distinct *Mahonia hybrida* plant characterized by the following characteristics:

(a) exhibits an upright growth habit, (b) forms attractive narrow deep green spiny foliage, (c) commonly forms yellow flowers in the spring extending into the summer and reblooms again in about August through frost, and (d) is well suited for providing attractive ornamentation in the landscape;

substantially as illustrated and described.

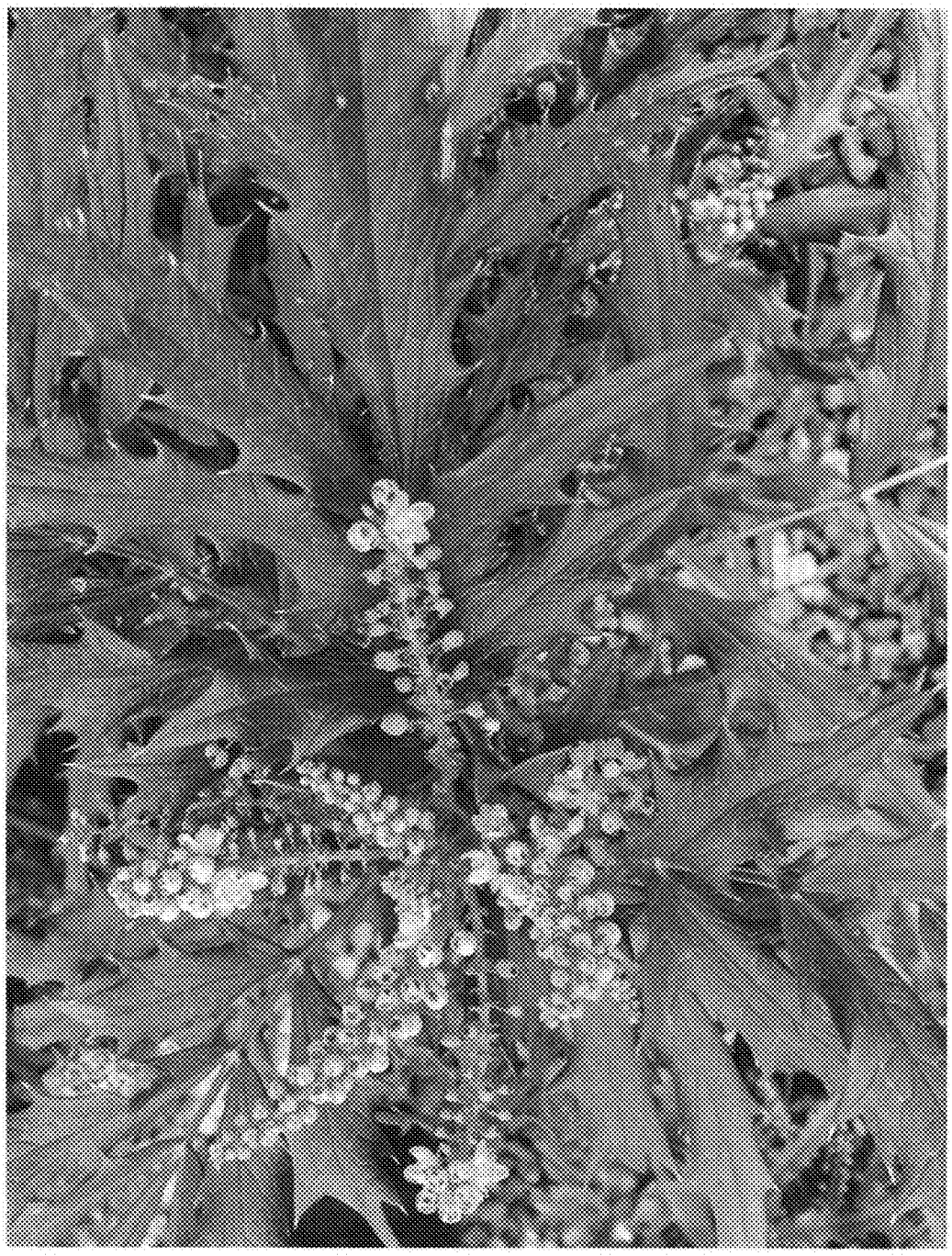

* * * * *